(12) United States Patent
Gupte

(10) Patent No.: US 6,284,790 B1
(45) Date of Patent: Sep. 4, 2001

(54) METHODS OF POTENTIATING ORGANIC NITRATES HAVING VASODILATING ACTIVITY AND FORMULATIONS FOR THE SAME

(76) Inventor: Sachin Gupte, 806 Old Farm Rd., Valhalla, NY (US) 10595

( * ) Notice: Subject to any disclaimer, the term of this patent is extended or adjusted under 35 U.S.C. 154(b) by 0 days.

(21) Appl. No.: 09/594,388

(22) Filed: Jun. 15, 2000

(51) Int. Cl.[7] ............... A61K 31/34; A61K 31/195; A61K 31/19; A61K 31/13

(52) U.S. Cl. ............... 514/470; 514/474; 514/562; 514/563; 514/568; 514/645

(58) Field of Search .................. 514/470, 474, 514/562, 563, 568, 645

(56) References Cited

U.S. PATENT DOCUMENTS

| | | |
|---|---|---|
| 4,808,627 | 2/1989 | Ogletree . |
| 4,839,384 | 6/1989 | Ogletree . |
| 5,122,384 | 6/1992 | Paradissis et al. . |
| 5,296,232 * | 3/1994 | Paradissis et al. .............. 424/451 |
| 5,462,726 | 10/1995 | Lodge . |
| 5,591,758 * | 1/1997 | Nallet et al. .............. 514/365 |
| 5,661,129 * | 8/1997 | Feelisch et al. .............. 514/19 |
| 5,767,160 | 6/1998 | Kaesemeyer . |
| 5,965,529 | 10/1999 | Garfield et al. . |
| 5,968,911 | 10/1999 | Lawson et al. . |

FOREIGN PATENT DOCUMENTS

| 9502408 | 1/1995 | (WO) . |
|---|---|---|

OTHER PUBLICATIONS

Akimoto et al., "Vasoinhibitory Effect of NP–252, a New Dihydropyridine Derivative, in Canine Cerebral Artery," Life Sciences, vol. 48, No. 2, pp. 183–188 (1991).

T. W. Anderson, "Vitamin E in Angina Pectoris," CMA Journal, vol. 110, pp. 401–406 (1974).

Anderson et al., "A Double–Bind Trial of Vitamin E in Angina Pectoris," American Journal of Clinical Nutrition, pp. 1174–1178 (1974).

Arstall et al, "N–Acetylcysteine in Combination with Nitroglycerin and Streptokinase for the Treatment of Evolving Acute Myocardial Infarction," Circulation, vol. 92, No. 10, pp. 2855–2862 (1995).

Bassenge et al., "Tolerance to Nitrates and Simultaneous Upregulation of Platelet Activity Prevented by Enhancing Antioxidant State," Nauny–Schmeideberg' Arch Pharmacol vol. 353, pp. 363–367 (1996).

Eglen et al., "RS–61756–007: A Potent and Selective Thromboxane Receptor (TP) Agonist, " J. Pharm. Pharmacol. vol. 41, pp. 347–349 (1989).

Uri Elkayam, "Prevention of Nitrate Tolerance with Concomitant Administration of Hydralazine," Can J Cardiol, vol. 12, Supp. C, pp. 17C–21C (1996).

Golino et al, "Failure of Nitroglycerin and Diltiazem to Reduce Platelet–Mediated Vasoconstriction in in Dogs with Coronary Artery Stenosis and Endothelial Injury: Further Evidence for Thromboxane $A_2$ and Sertonin as Mediators of Coronary Artery Vasoconstriction in Vivo,"JACC, vol. 15, No. 3, pp. 718–726 (1990).

Gupte et al., "Coronary Vasoconstriction in Superoxide–Pretreated Rat Heart," Proc. Japan Acad., vol. 71B, pp. 274–278 (1995).

Gupte et al., "Superoxide and Nitroglycerin Stimulate Release of $PGF_2$ and $TxA_2$ in Isolated Rat Heart, " American Physiological Society, pp. H2447–H2453 (1996).

Gupte et al., "NADPH and Heme Redox Modulate Pulmonary Artery Relaxation and Guanylate Cyclase Activation by NO," American Physiological Society, pp. L1124–L1132 (1999).

Gupte et al., "Regulation of NO–Elicited Pulmonary Artery Relaxation and Guanylate Cyclase Activation by NADH Oxidase and SOD," American Physiological Society, pp. H1535–H1542 (1999).

Gupte Activation of $TXA_2/PGH_2$Receptors and Protein Kinase C Contribute to Coronary Dysfunction in Superoxide Treated Rat Hearts, J. Mol Cell Cardiol, vol. 32, pp. 937–946 (2000).

Hall et al., 9, 11–Epoxy–9–Homo–14–Thiaprost–5–Enoic Acid Derivatives: Potent Thromboxane $A_2$ Antagonists, J. Med. Chem. vol. 32, pp. 974–984 (1989).

Hinz et al., "Vitamin C Attenuates Nitrate Tolerance Independently of its Antioxidant Effect," FEBS Letters, vol. 428, pp. 97–99 (1998).

Iesaki et al., "A Flavorprotein Mechanism Appears to Prevent an Oxygen–Dependent Inhibition of cGMP–Associated Nitric Oxide–Elicited Relaxation of Bovine Coronary Arteries," Circulation Research, vol. 85, pp. 1027–1031, (1999).

Iesaki et al., "Inhibition of Guanylate Cyclase Stimulation by NO and Bovine Arterial Relaxation to Peroxynitrite and $H_2O_2$," American Physiological Society, pp. H978–H985 (1999).

Ito et al., "Comparison of Effects of Ascorbic Acid on Endothelium–Dependent Vasodilation in Patients with Chronic Congestive Heart Failure Secondary to Idiopathic Dilated Cardiomyopathy Versus Patients with Effort Angina Pectoris Secondary to Coronary Artery Disease," AM J. Cardiol, vol. 82, pp. 762–767 (1998).

(List continued on next page.)

Primary Examiner—Raymond Henley, III
(74) Attorney, Agent, or Firm—Baker Botts

(57) ABSTRACT

A method for potentiating an organic nitrate having vasodilating activity by administering to a subject an effective amount of the organic nitrate with a potentiating amount of a thromboxane receptor antagonist and a reducing agent. Formulations and synergistic compositions are also described.

45 Claims, 6 Drawing Sheets

OTHER PUBLICATIONS

Levine et al., "Ascorbic Acid Reverses Endothelial Vasomotor Dysfunction in Patients with Coronary Artery Disease," Circulation, vol. 93, pp. 1107–1113 (1996).

William G. Mayhan, "Role of Prostaglandin $H_2$–Thromboxane $A_2$ in Responses of Cerebral Arterioles During Chronic Hypertension," American Physiological Society, pp. H539–H543 (1992).

Alan L. Miller, "Botanical Influences on Cardiovascular Disease," Alternative Medicine Review, vol. 3, No. 6, pp. 422–431 (1998).

Minkes et al., "Influence of SQ 29, 548 on Vasoconstrictor Responses in the Mesenteric Vascular Bed of the Cat, " European Journal of Pharmacology, vol. 179, pp. 119–127 (1990).

Münzel et al., "Neurohormonal Activation and Nitrate Tolerance: Implications for Concomitant Therapy with Angiotensin–Converting Enzyme Inhibitors or Angiotensin Receptor Blockers, " AM J. Cardiol, vol. 81, No. 1A, pp. 30A–40A (1998).

Ritter et al., "Effects of a Selective Thromboxane Receptor Antagonist (GR32191B) and of Glyceryl Trinitrate on Bleeding Time in Man," Br. J. Clin. Pharmac., vol. 29, pp. 431–436 (1990).

Watanabe et al., "Randomized, Double–Blind Placebo–Controlled Study of Supplemental Vitamin E on Attenuation of the Development of Nitrate Tolerance," Circulation, vol. 96, pp. 2545–2550 (1997).

Watanabe et al., "Randomized Double–Blind, Placebo–Controlled Study of Carvedilol on the Prevention of Nitrate Tolerance in Patients with Chronic Heart Failure,"JACC, vol. 32, No. 5, pp. 1194–1200 (1998).

Watanabe et al., "Randomized Double–Blind, Placebo–Controlled Study of the Preventive Effect of Supplemental Oral Vitamin C on Attenuation of Development of Nitrate Tolerance,"JACC, vol. 31, No. 6, pp. 1323–1329 (1998).

Watanabe et al., "Preventive Effects of Carvedilol on Nitrate Tolerance –A Randomized, Double–Blind, Placebo–Controlled Comparative Study Between Carvedilol and Arotinolol," JACC, vol.32, No. 5, pp. 1201–1206 (1998).

Watanabe et al., "Randomized Double–Blind, Placebo–Controlled Study of Supplemental Vitamin E on Attenuation of the Development of Nitrate Tolerance," vol. 31, No. 3, pp. 173–181 (1998).

Watanabe et al., "Antioxidants and Nitrate Tolerance"response by Watanabe et al., Circulation, vol. 98, No. 13, p. 1350 (1998).

* cited by examiner (A) CONTROL
(B) 4μM NTG
(C) 100μM NADPH
(D) 4μM NTG AND 100μM NADPH
(E) 10μM ONO-3708
(F) 4μM NTG, 10μM ONO-3708 AND 100μM NADPH

METHODS OF POTENTIATING ORGANIC NITRATES HAVING VASODILATING ACTIVITY AND FORMULATIONS FOR THE SAME

FIELD OF THE INVENTION

The present invention relates to methods and formulations for potentiating the vasodilating activity of organic nitrates being administered to a subject, and more particularly, to methods and formulations for potentiating the vasodilating activity of nitroglycerin.

BACKGROUND OF THE INVENTION

For over one hundred years, organic nitrates such as nitroglycerin and amyl nitrite, among others, have been used to relieve anginal pain and treat heart disease (Reeves. J. T., 1995, NIPS. 10, 141). The beneficial use of these compounds is due to their ability; once administered to subject, to induce dilation of the vascular system (i.e., arteries and veins) resulting in decrease in blood pressure and attenuation of the pre-load on the heart.

Nitroglycerin or glycerol trinitrate is an organic nitrate ester which, when administered to a subject, is converted biologically to nitric oxide ("NO"), a pharmacologically active metabolite. NO, for example, activates soluble guanylate cyclase in vascular smooth muscle cells which in turn increases cyclic guanosine monophosphate (cGMP) resulting in vasorelaxation and ultimately leading to vasodilation and a reduction in blood pressure. However, the effectiveness of nitroglycerin and other organic nitrates having vasodilating activity is greatly diminished because the recipient of the organic nitrate rapidly develops a tolerance to the beneficial effects of the organic nitrate.

Tolerance to the vascular and anti-anginal effects of nitroglycerin and other organic nitrates can develop at low dosages as well as at high dosages. As a result, the organic nitrate loses its effectiveness during sustained therapy and increasing amounts of the organic nitrate must be administered to achieve the same effect. As nitrate tolerance progresses, the effectiveness of nitroglycerin and other organic nitrates are further limited and increased dosages have little or no effect on vasorelaxation or vasodilation (see, e.g., Bogaert, M., 1991, J. Cardiovas. Pharmacol. 17 (Suppl. 3), S313; and Unger, P., et al., 1991, J. Cardiovasc. Pharmacol. 17 (Suppl. 3), S300). Furthermore, in certain circumstances, the administration of an organic nitrate to a patient who is nitrate tolerant may result in vasoconstriction, and not vasodilation (Caramori et al., 1998, JACC 32(7), 1969; Gupte et al., 1996, Am. J. Physiol. H2447). This is potentially a dangerous side effect as the administration of the organic nitrate may exacerbate the very condition that it is supposed to improve. Moreover, the infusion of very high doses of organic nitrates in an attempt to overcome the development of tolerance may lead cytotoxicity and organ failure.

The precise mechanism in which tolerance of organic nitrates (e.g., nitroglycerin) develops remains unknown. Theories explaining the development of tolerance include: (1) the sulfhydryl pools necessary for the direct biotransformation of nitroglycerin into active nitric oxide are depleted by excess nitroglycerin substrate (Boesgaard, S., et al., 1991, J. Pharmacol. Exp. Ther. 258, 851); (2) the activation of vascular guanylate cyclase is diminished by nitroglycerin (Henry P. J., et al., 1989, Br. J. Pharmacol. 98, 757); or (3) the rate of cGMP degradation may be increased due to enhanced of cGMP phosphodiesterase during tolerance to nitroglycerin (Axelsson, K. L., et al., 1987, Drugs 33, 63). Additionally, neurohormonal activation and increase in plasma volume have recently been incriminated in tolerance development.

Attempts to avoid or reduce the development of nitrate tolerance have included the use of antioxidants such as vitamins E and C. (Munzel et al., 1998, Am. J. Cardiol. 81 (1A), 30A). Other methods include the administration of reduced glutathione or cysteine and the pretreatment with angiotensin II converting enzyme inhibitors or angistensin II receptor antagonist. Likewise, some success has been achieved with thromboxane receptor antagonists to inhibit vasoconstriction associated with organic nitrate administration (Gupte et al., 1996, Am. J. Physiol. H2447). However, these methods have produced conflicting results.

In view of the above, and because nitrates are considered as first-line therapy, there is a need in the art for methods of potentiating (i.e., increasing the effectiveness of) organic nitrates being administered to subject who does not exhibit a tolerance for organic nitrates. Likewise, there is a need in the art for methods of increasing the effectiveness of organic nitrates being administered to a subject who already exhibits a tolerance to organic nitrates.

Accordingly, it is an object of the present invention to provide, inter alia, methods, formulations, and synergistic compositions for potentiating of organic nitrates being administered to a subject.

SUMMARY OF THE INVENTION

The present invention provides a method for potentiating an organic nitrate having vasodilating activity by administering to a subject an effective amount of the organic nitrate with a potentiating amount of a thromboxane receptor antagonist and a reducing agent. In one embodiment, the organic nitrate, thromboxane receptor antagonist and reducing agent are co-administered to the subject. In alternative embodiment, the thromboxane receptor antagonist and reducing agent are administered to the subject prior to the organic nitrate. While in another embodiment, the organic nitrate is administered to the subject prior to the thromboxane receptor antagonist and reducing agent. The subject preferably is a mammal, which may be in need of vasodilation and may additionally exhibit a tolerance for the organic nitrate.

An organic nitrate having vasodilating activity includes nitroglycerin, amyl nitrite, isosorbide dinitrate, isosorbide mononitrate, erythrityl tetranitrate, pentaerythritol trinitrate, pentaerythritol tetranitrate, sodium nitroprusside, trolnitrate phosphate, clonitrate, mannitol hexanitrate, propatyl nitrate, or any mixture thereof. One preferred organic nitrate is nitroglycerin. An effective amount of the organic nitrate ranges from 0.0001 to 120 mg/kg of body weight per day, with no more than 30 mg/kg being preferred, and no more 0.5 mg/kg being more preferred.

In one embodiment the reducing agent is a non-antioxidant reducing agent. Non-antioxidant reducing agent include GDP (guanosine diphosphate), GTP (guanosine triphosphate), NADPH (reduced nicotinamide-adenine dinucleotide phosphate), NADH (reduced nicotinamide-adenine dinucleotide), $FADH_2$ (reduced flavin-adenine dinucleotide), $FMNH_2$ (reduced flavin mononucleotide), sodium pyruvate, sodium dithionite, N-acetylcysteine, reduced glutathione or any mixture thereof. In another embodiment, the reducing agent is L-ascorbic acid.

Thromboxane receptor antagonists include ONO-3708, Seratrodast, Rodigrel, Daltroban, Sulotroban, AH 23848, GR 32191, ICI 192605, SQ 28668, SQ 28913, SQ 29548, or any mixture thereof. Two preferred thromboxane receptor antagonists are ONO-3708 and Seratrodast.

In accordance with the invention, the potentiating amount of the thromboxane receptor antagonist and reducing agent provide at least a 15% decrease in the coronary perfusion pressure of the subject as compared to the organic nitrate alone. More preferable, the potentiating amount provides at least a 25% decrease, with at least a 40% or greater decrease in coronary perfusion pressure being preferred.

The present invention also provides a formulation for inducing vasodilation which includes an effective amount of the organic nitrate and a potentiating amount of the thromboxane receptor antagonist and the reducing agent. Potentiating amounts for the formulation are an organic nitrate:thromboxane receptor antagonist ratio of 1:1 to 1:2000, and an organic nitrate:reducing agent ratio of 1:10 to $1:5 \times 10^7$. Preferable are organic nitrate:thromboxane receptor antagonist ratios of 1:1 to 1:1000, and organic nitrate:reducing agent ratios of 1:10 to $1:5 \times 10^5$ with organic nitrate:thromboxane receptor antagonist ratios of 1:1 to 1:100, and organic nitrate:reducing agent ratio of 1:10 to $1:5 \times 10^3$ being more preferred. In another embodiment, the formulation further includes a physiologically-acceptable carrier.

A synergistic composition for potentiating the organic nitrate is also provided. The synergistic composition includes the thromboxane receptor antagonist and the reducing agent. The composition contains the thromboxane receptor antagonist and reducing agent in a ratio ranging from 1:1 to $1:5 \times 10^7$, with 1:1 to $1:5 \times 10^5$ being preferred, and 1:1 to $1:5 \times 10^3$ being more preferred. In another embodiment, the composition further includes a physiologically-acceptable carrier.

Through the present invention, improved vasodilating activity from organic nitrates are achieved. Significant decreases in coronary perfusion pressure are facilitated by the combined use of the thromboxane receptor antagonist and reducing agent. Likewise, the present invention facilitates the use reduced dosages of organic nitrates to achieve levels of vasodilation that were previously obtained with significantly higher dosages. These and other advantages will be readily apparent from the detailed description of the invention set forth below.

DETAILED DESCRIPTION OF THE INVENTION

Figure 1:
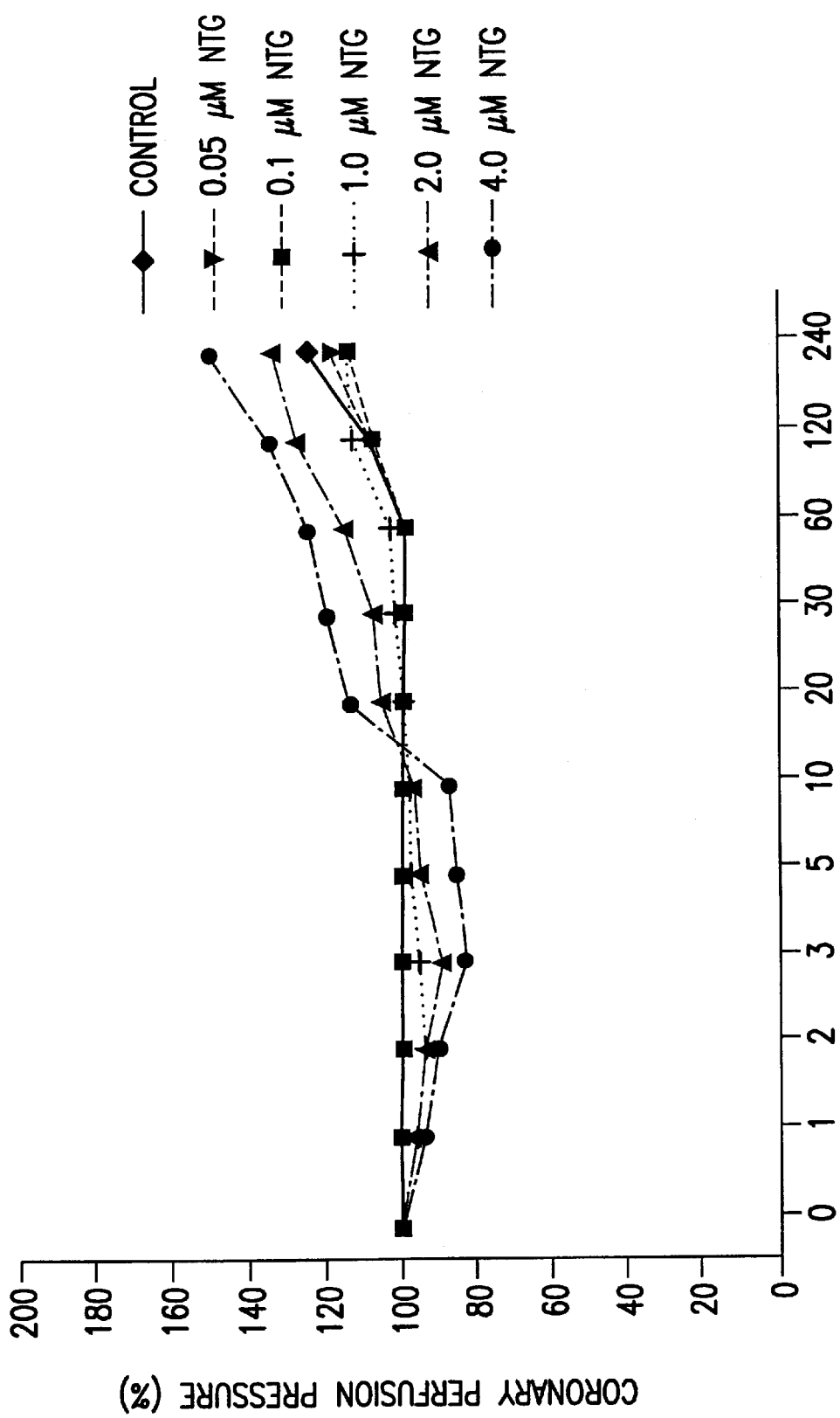
FIG. 1 is a line graph illustrating the effect on coronary perfusion pressure ("CPP") by the administration of varying concentrations of nitroglycerin ("NTG").

In accordance with the present invention, a method for potentiating the vasodilating activity of organic nitrates is provided. Advantageously, the vasodilating activity of organic nitrates is potentiated (i.e., increased) by administering the organic nitrate in conjunction with a thromboxane receptor antagonist and a reducing agent. The unexpected synergism between the organic nitrate and the combination of the thromboxane receptor antagonist and reducing agent facilitates the use of reduced levels of organic nitrates to achieve sufficient vasodilation in a subject.

A subject in this context means any organism, preferably living, with mammals being more preferred. Representative examples of mammals include, but are not limited to, bovines, canines, felines, equines, murines and humans. In another preferred embodiment, the subject (e.g., a mammal) is in need of vasodilation, which means that the subject is suffering from cardiac or other conditions in which vasodilation would provide some beneficial relief from or amelioration of unwanted symptoms due to the condition (e.g., chest pain due to angina pectoris). In another embodiment, the subject exhibits already exhibits a tolerance for organic nitrates having vasodilating activity.

In accordance with the present invention, the sequence by which the organic nitrate, thromboxane receptor antagonist and reducing agent are administered to a subject is variable. In a preferred embodiment, the organic nitrate, thromboxane receptor antagonist and reducing agent are co-administered to the subject for ease of delivery. Alternatively, the thromboxane receptor antagonist and reducing agent are administered to the subject prior to the organic nitrate or in the reverse order. In yet another embodiment, the organic nitrate, thromboxane receptor antagonist, and reducing agent are administered sequentially to each other or with the organic nitrate and either thromboxane receptor antagonist or reducing agent being co-administered. The preferred sequence of administration for any particular formulation can easily be determined by one skilled in the art following the teachings of the invention.

The organic nitrate can be any organic nitrate (or nitrite) having vasodilating and/or anti-anginal activity. Vasodilating activity in this context means that the compound is capable of increasing the diameter of the blood vessels in a subject thereby decreasing the resistance to blood flow. As will be apparent to those skilled in the art, the decrease in resistance to blood flow can be approximated by measuring the decrease in coronary perfusion pressure ("CPP") which is the pressure needed to infuse fluid into the heart.

Examples of organic nitrates (or nitrites) have vasodilating activity and/or antianginal activity are well known in the art. Representative example of suitable organic nitrates having vasodilating activity to be utilized in accordance with the present invention include, but are not limited to, nitroglycerin, amyl nitrite, isosorbide dinitrate, isosorbide mononitrate, erythrityl tetranitrate, pentaerythritol trinitrate, pentaerythritol tetranitrate, sodium nitroprusside, trolnitrate phosphate, clonitrate, mannitol hexanitrate, propatyl nitrate, or mixtures thereof. One preferred organic nitrate is nitroglycerin.

In accordance with the invention, an effective amount of an organic nitrate having vasodilating activity is administered to a subject. An effective amount is an amount of the organic nitrate sufficient to induce a decrease in the CPP of the subject. Changes in a subject's CPP can be monitored by non-invasive techniques such as Doppler- and echo-cardiography. Likewise, changes in a subject's CPP can be indirectly ascertained by measuring blood pressure (plethsmography). However, other methods can be used to ascertain a decrease in a subject's CPP due to vasodilation from organic nitrate administration.

The amount of the organic nitrate needed to induce a decrease in CPP will vary from subject to subject and is affected by a variety of factors, including the $ED_{50}$ (or $IC_{50}$) of the specific organic nitrate, the method of administration, the body mass and age of the subject, and the existence of nitrate tolerance. In general, an effective amount of the organic nitrate will range from 0.0001 to 120 mg/kg of body weight per day, with an upper limit of 30 mg/kg being preferred, and an upper limit of 0.5 mg/kg being more preferred. For example, in the case of nitroglycerin, the dosages can vary from 0.3–0.6 mg for tablet form, 15–30 mg for an ointment, 0.1–10 mg/hr for a transdermal patch and 0.5–75 $\mu$g/kg/min for an intravenous solution. The above parameters can be easily ascertained by one of ordinary skill in the art.

As previously described, the thromboxane receptor antagonist and a reducing agent are utilized to potentiate the organic nitrate. Thromboxane receptor antagonists to be used in accordance with the invention are any selective thromboxane $A_2$-receptor antagonist. Examples of thromboxane receptor antagonists are well known in the art. Representative examples to be used include, but are not limited to, ONO-3708 ((9,11),(11,12)-dideoxa-9 alpha, 11 alphadimethylmethano-11,12-methano-13,14-dihydro-1 3-aza-1 4-oxo-15-cyclopenthyl-16,17,18,19,20-penthanol-15-epi-TxA$_2$), Seratrodast (($\pm$)-$\zeta$-(2,4,5-trimethyl-3,6-dioxo-1,4-cyclohexadien-1-yl)benzene heptanoic acid), Rodigrel ((E)-5-[[[3-pyridinyl[3-(trifluoromethyl)phenyl]methylene]amino]oxy]pentanoic acid), Daltroban (4-[2-[[(4-chlorophenyl)sulfonyl]amino]ethyl]-benzeneacetic acid), Sulotroban (4-[2-(benzenesulfamido)ethyl] phenoxyacetic acid), AH 23848 ([1$\alpha$(Z)-2$\beta$,5$\alpha$]-(+)-7-[5-[[(1,1'-biphenyl)-4-yl]-methoxy]-2-(4-morpholinyl)-3-oxo-cyclopentyl]-4-heptanoic acid), GR 32191 ([1R-[1$\alpha$(Z),2$\beta$, 3$\beta$,5$\alpha$]]-(+)-7-[5-([1,1'-biphevyl]-4ylmethoxy)-3hydroxy-2-(1-piperidinyl)cyclopentyl]-4-heptanoic acid), ICI 192605-4 ((Z)-6-[(2,4,5-cis)2-chlorophenyl)-4-(2-hydroxyphenyl)1,3-dioxan-5-yl]hexanoic acid, SQ 28668 ([1S-[1$\alpha$,2$\beta$(5Z),3$\beta$(1E,3R,4S),4$\alpha$]]-7-[3-(3-hydroxy-4-phenyl-1-pentenyl)-7-oxabicyclo[2.2.1]-hept-2-yl]-5-heptenoic acid), SQ 28913 ([S-[1$\alpha$,2$\alpha$(Z),3$\alpha$, 4$\alpha$]]-7-[3-[(hexylthio)methyl]-7-oxabicyclo[2.2.1]hept-2-yl]-5-heptenoic acid), SQ 29548 ([1S-[1$\alpha$,2$\alpha$,(Z),3$\alpha$(1E,3S*, 4R*),4$\alpha$]]-7-[3-(3-hydroxy-4-phenyl-1-pentenyl)-7-oxabicyclo[2.2.1]hept-2-yl]-5-heptenoic acid) and any mixture thereof. Preferred thromboxane receptor antagonist are ONO-3708 and Seratrodast.

In the context of the present invention, a reducing agent is any compound capable of reducing the valency of another compound and is itself oxidized as a result of donating electrons (i.e., the compound is an electron donor). Preferably, the compound is physiologically-acceptable to the subject which means the compound is generally tolerable (i.e., relatively non-toxic). The reductive ability of a compound is often characterized by measuring its redox potential ($E_o$). This is in contrast to a "classic" antioxidant that neutralizes free radicals by either trapping the free radical or by acting as a free radical scavenger. However, as will be apparent to those skilled in the art, some compounds characterized as antioxidants also function as reducing agents (i.e., electron donors). In accordance with the present invention, the reducing agent of the synergistic composition includes non-antioxidant reducing agents and antioxidants that have reductive properties. Examples of non-antioxidant reducing agents include GDP, GTP, NADPH, NADH, $FADH_2$, $FMNH_2$, sodium pyruvate, sodium dithionite, N-acetylcysteine, reduced glutathione, or mixtures thereof. An example of an antioxidant having reductive properties is L-ascorbic acid. Combinations of two categories of compounds can also be used. In a preferred embodiment, the reducing agent is L-ascorbic acid or NADPH.

The thromboxane receptor antagonist and reducing agent are administered in a potentiating amount to synergize the vasodilating effect of the organic nitrate. A potentiating amount in this context means an amount of the thromboxane receptor antagonist and reducing agent sufficient to increase the vasodilating effect of the organic nitrate so as to induce at least 15 percent decrease in CPP as compared to the decrease exhibited by the administration of the organic nitrate alone. Preferably, the potentiating amount is an amount that provides at least a 25 percent decrease in CPP, with at least 40 percent or greater being more preferred. One distinct advantage of the present invention is that low dosages of organic nitrates that do not exhibit sufficient vasodilation when administered alone can now provide effective levels of vasodilation when administered with the thromboxane receptor antagonist and reducing agent. Accordingly, significantly reduced levels of organic nitrates can be used to provide sufficient vasodilation to a subject.

As will be apparent to one skilled in the art, the ratio of organic nitrate to thromboxane receptor antagonist and reducing agent to provide a potentiating amount is variable. Generally, the amount of the thromboxane receptor antagonist is substantially less than the reducing agent. In accordance with the present invention, the molar ratio of the organic nitrate to the thromboxane receptor antagonist ranges from 1:1 to 1:2000, with 1:1 to 1:1000 being preferred, and 1:1 to 1:100 being more preferred. The molar ratio of the organic nitrate to the reducing agent ranges from 1:10 to 1:5$\times$10$^7$, with 1:10 to 1:5$\times$10$^5$ being preferred, and 1:10 1:5$\times$10$^3$ being more preferred. In addition, the choice of thromboxane receptor antagonist and reducing agent will affect ratio of two components needed to provide optimum potentiation. For example, the efficacy of thromboxane receptor antagonists as characterized by their respective $ED_{50}$ (or $IC_{50}$) will vary from compound to compound. Likewise, the efficacy of reducing agents as characterized by their respective redox potentials will also vary from compound to compound. These parameters can be easily ascertained by one of ordinary skill in the art following the teachings of the present invention.

The present invention also provides formulations for inducing vasodilation in subject, which includes an effective amount of the organic nitrate having vasodilating activity and a potentiating amount of the thromboxane receptor antagonist and reducing agent. The formulations of the invention are administered to a subject by any technique known in the art. Routes of delivery can include, but are not limited to, oral, intranasal, sublingual, intrapulmonary, rectal, transdermal, intravenous and combinations thereof. Acceptable dosage forms suitable for administration to a subject include, but are not limited to, tablets, capsules, powders, patches, solutions, suspensions, immediate and sustained release. Preferably, the formulations of the invention include a physiologically-acceptable carrier in which the organic nitrate is dispersed. For example, the carrier can be buffered saline if a liquid formulation is prepared. Procedures for making and administering such dosage forms are well within the abilities of one of ordinary skill in the art.

In addition, the present invention provides a synergistic composition for potentiating an organic nitrate having vasodilating activity. The synergistic composition includes the thromboxane receptor antagonist and the reducing agent. The molar ratio of the thromboxane receptor antagonist to reducing agent in the synergistic composition ranges from 1:1 to $1:5\times10^7$, with 1:1 to $1:5\times10^5$ being preferred and 1:1 to $1:5\times10^3$. The synergistic composition is administered and formulated is the same manner as the organic nitrate containing formulations described above.

The following non-limiting examples illustrate the use of organic nitrates in conjunction with thromboxane receptors antagonists and reducing agents to provide vasodilation.

EXAMPLES

Comparative Example 1

Male Sprague-Dawely rats weighing 310 to 400 grams were decapitated and the hearts were quickly excised. Langendorff perfusion was established following the procedure described in Gupte, S. A., Okada, T., Ochi, R., "Coronary vasoconstriction in superoxide-pre-treated rat heart: increase by nitroglycerin and decrease by NO synthase inhibitors" Proc. Jpn. Acad. Ser. B.71:1995, p. 274–278 and in Okada, T., "Hypoxia-induced changes in prostanoids production and coronary flow in isolated rat heart", J. Mol. Cell Cardiol. 23:939–948 (1991), which are incorporated by reference.

Each heart was perfused retrogradely with modified Krebs-Henseleit solution containing 116 mM NaCl, 25 mM $NaHCO_3$, 2.5 mM $CaCl_2$, 1.2 mM $MgSO_4$, 4.7 mM KCl, 1.2 mM $KH_2PO_4$, and 5.5 mM glucose (pH 7.4) at a constant flow rate of 12 mL/minute without re-circulation. The perfusate was warmed to 38° C. and oxygenated with a 95%, 2–5% $CO_2$ gas mixture to maintain an $O_2$ pressure greater than 400 mm Hg during the entire experimental period. Changes in the mean coronary perfusion pressure ("CPP") were monitored by placing a water transducer at the entrance of the perfusate into the coronary arteries. CPP at time=0 was considered control and deemed to be 100%.

After a 15 to 20 minute stabilization and control period, the coronary flow was increased to 24 mL/min to maintain the CPP between 85–95 mm Hg. The hearts were perfused with the elevated flow for 10 minutes. After perfusion for 10 minutes at the elevated flow rate, the hearts were ready to be perfused with the test compounds.

In order to ascertain the vasodilating activity of nitroglycerin ("NTG"), the following concentrations of NTG were administered (n=4–7): 0.05 $\mu$M; 0.1 $\mu$M; 1.0 $\mu$M; 2.0 $\mu$M; and 4.0 $\mu$M, which correlate to intravenous dosages of about 0.681 $\mu$g/kg; 1.362 $\mu$g/kg; 13.62 $\mu$g/kg; 27.252 $\mu$g/kg; and 54.504 $\mu$g/kg, respectively. Changes in the CPP were monitored and are shown in FIG. 1 and listed in Table 1.

As can be seen from FIG. 1 and Table 1, 0.05 $\mu$M NTG(—▼—), 0.1 $\mu$M NTG(—■—) and 1.0 $\mu$M NTG(—+—) had a minimal impact on coronary perfusion pressure. In fact, perfusion with 0.05 $\mu$M NTG and 0.1 $\mu$M NTG provided no vasodilation at all. Perfusion with 2.0 $\mu$M NTG(—▲—) and 4 $\mu$M NTG (—●—) resulted in a transient decrease in perfusion pressure. However, within 20 minutes following the administration of 2.0 $\mu$M NTG and 4.0 $\mu$M NTG, the CPP increased above 100%.

Comparative Example 2

Figure 2:
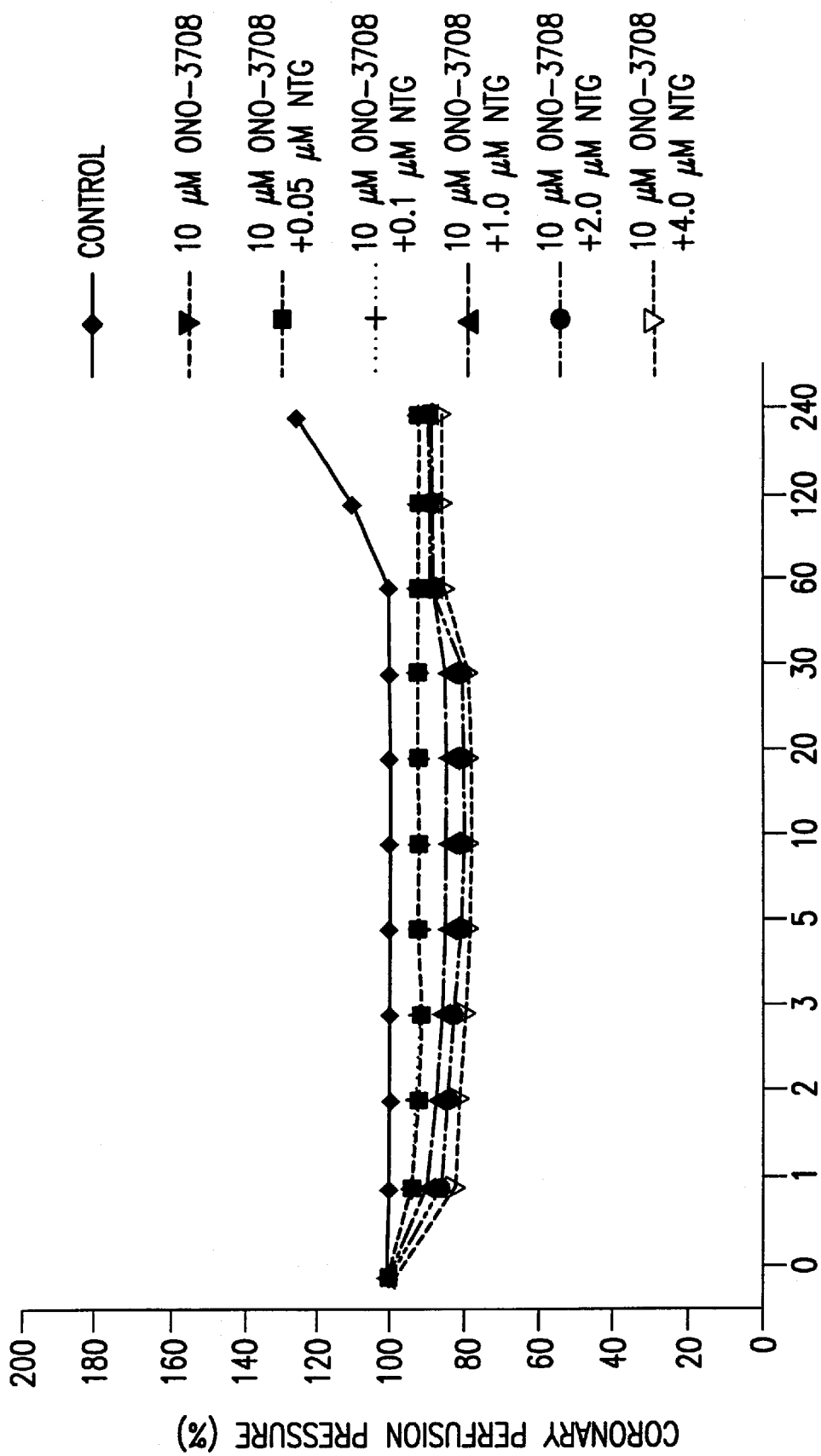
FIG. 2 is a line graph illustrating the effect on coronary perfusion pressure by varying concentrations of nitroglycerin administered with a thromboxane receptor antagonist, ONO-3708.

Following the procedure of Example 1, the vasodilating activity of nitroglycerin co-administered with a thromboxane receptor antagonist was ascertained. After the rat hearts were perfused with the elevated flow rate for 10 minutes, NTG and ONO-3708 were co-administered (n=4–6). The effect of the co-administration of 10 $\mu$M ONO-3708 (which correlates to an intravenous dosage of about 162 $\mu$g/kg), and the varying concentrations of NTG on CPP, are shown in FIG. 2 and listed in Table 1. A 10 $\mu$M ONO-3708 was used since this concentration correlates to the $IC_{50}$ for suppressing vasoconstriction induced with U46619, a thromboxane $A_2$ receptor analogue.

FIG. 2 illustrates that co-administration of ONO-3708 and NTG resulted in slight decrease in CPP. For example, the CPP dropped to only 91% when 0.05 $\mu$M NTG and 10 $\mu$M of ONO-3708 was administered(—■—). Increasing the NTG concentration to 1.0 $\mu$M (—+—) resulted in a CPP of 92%. Thus, the administration 0.05 $\mu$M, 0.1 $\mu$M and 1.0 $\mu$M NTG in fact provided no improvement over the administration of ONO-3708 alone (—▼—). However, the co-administration of ONO-3708 with either 2 $\mu$M NTG(—●—) or 4 $\mu$M NTG (—▼—) did prevent the vasoconstriction that occurred when 2 $\mu$M or 4 $\mu$M of NTG was administered alone (FIG. 1, —▲— & —●—).

Comparative Example 3

In order to ascertain the effect of L-ascorbic acid, an antioxidant having reducing properties, on the vasodilating activity of nitroglycerin, varying dosages of NTG were co-administered with L-ascorbic acid using the procedure described in Example 1. A concentration of 10 mM L-ascorbic acid was used, which correlates to an intravenous dosage of about 60 mg/kg. After the rat hearts were perfused with the elevated flow rate for 10 minutes, the NTG and L-ascorbic acid ("AA") were co-administered (n=5). The effect of the co-administration of L-ascorbic acid and varying concentrations of NTG on CPP, are shown in FIG. 3 and listed in Table 1.

Figure 3:
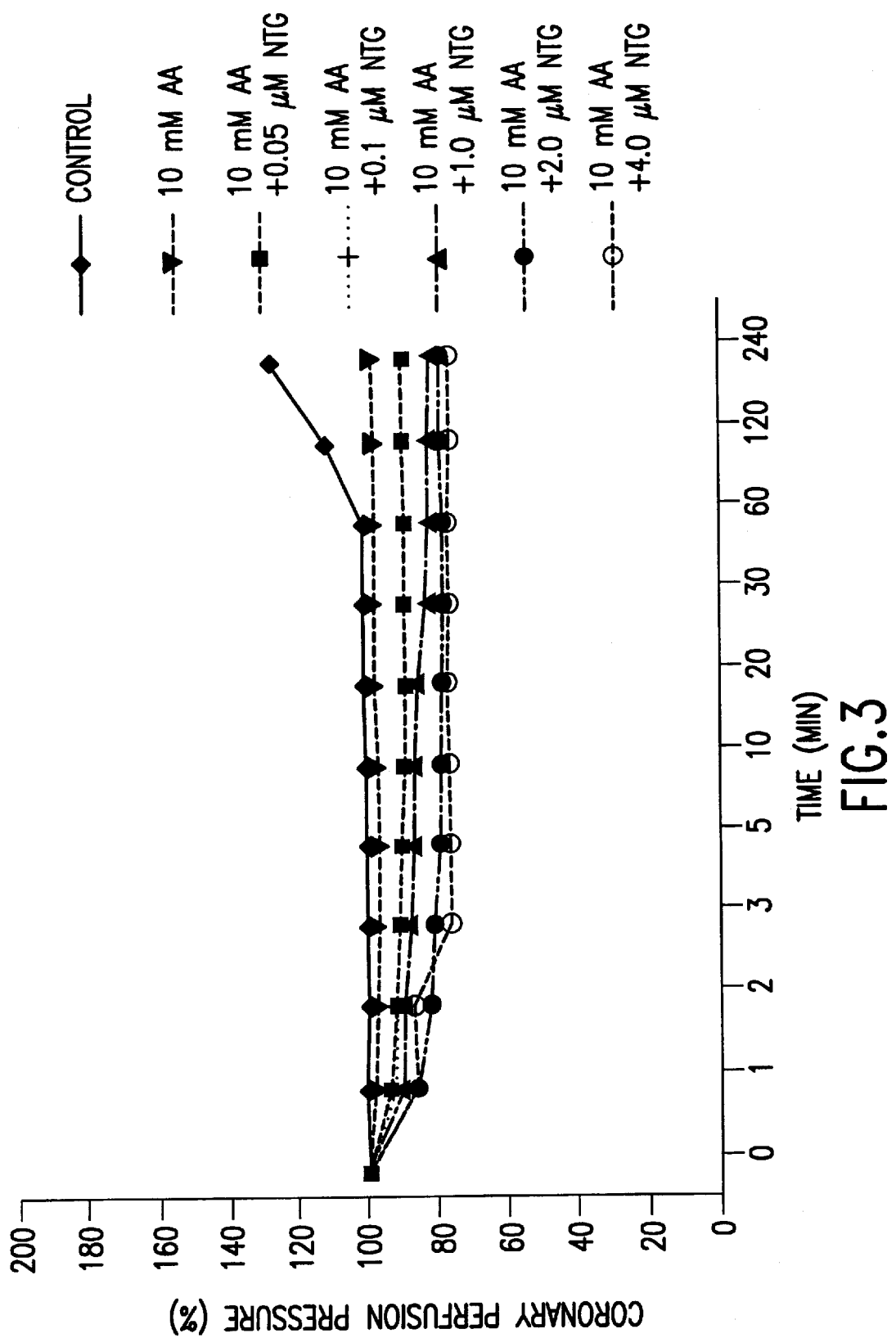
FIG. 3 is a line graph illustrating the effect on coronary perfusion pressure by varying concentrations of nitroglycerin administered with L-ascorbic acid ("AA") as a reducing agent.

FIG. 3 shows that co-administration of L-ascorbic-acid and NTG resulted in slight decrease in CPP. For example, the CPP dropped to only 88% 20 minutes after the administration of 0.05 $\mu$M NTG and 10 mM of ascorbic acid (—■—) or 0.1 $\mu$M NTG and 10 mM of L-ascorbic acid (—+—), which is a slight improvement over the administration of L-ascorbic acid alone (—▼—). Increasing the NTG concentration to 2.0 $\mu$M (—●—) and 4.0 $\mu$M (—○—) resulted in a CPP of 78% and 76%, respectively. Thus, the co-administration of L-ascorbic acid and NTG did provide some increased vasodilation and inhibited the vasoconstriction that was observed when NTG was administered alone.

Example 4

Following the procedure of Example 1, the vasodilating activity of nitroglycerin co-administered with the thromboxane receptor antagonist, ONO-3708, and the reducing agent, L-ascorbic acid, was ascertained. After the hearts were perfused with the elevated flow rate for 10 minutes, NTG was co-administered with a combination of ONO-3708 and L-ascorbic acid (n=6). The effects of co-administering ONO-3708 and L-ascorbic acid with varying concentrations of NTG on CPP, are shown in FIG. 4 and listed in Table 1.

Figure 4:
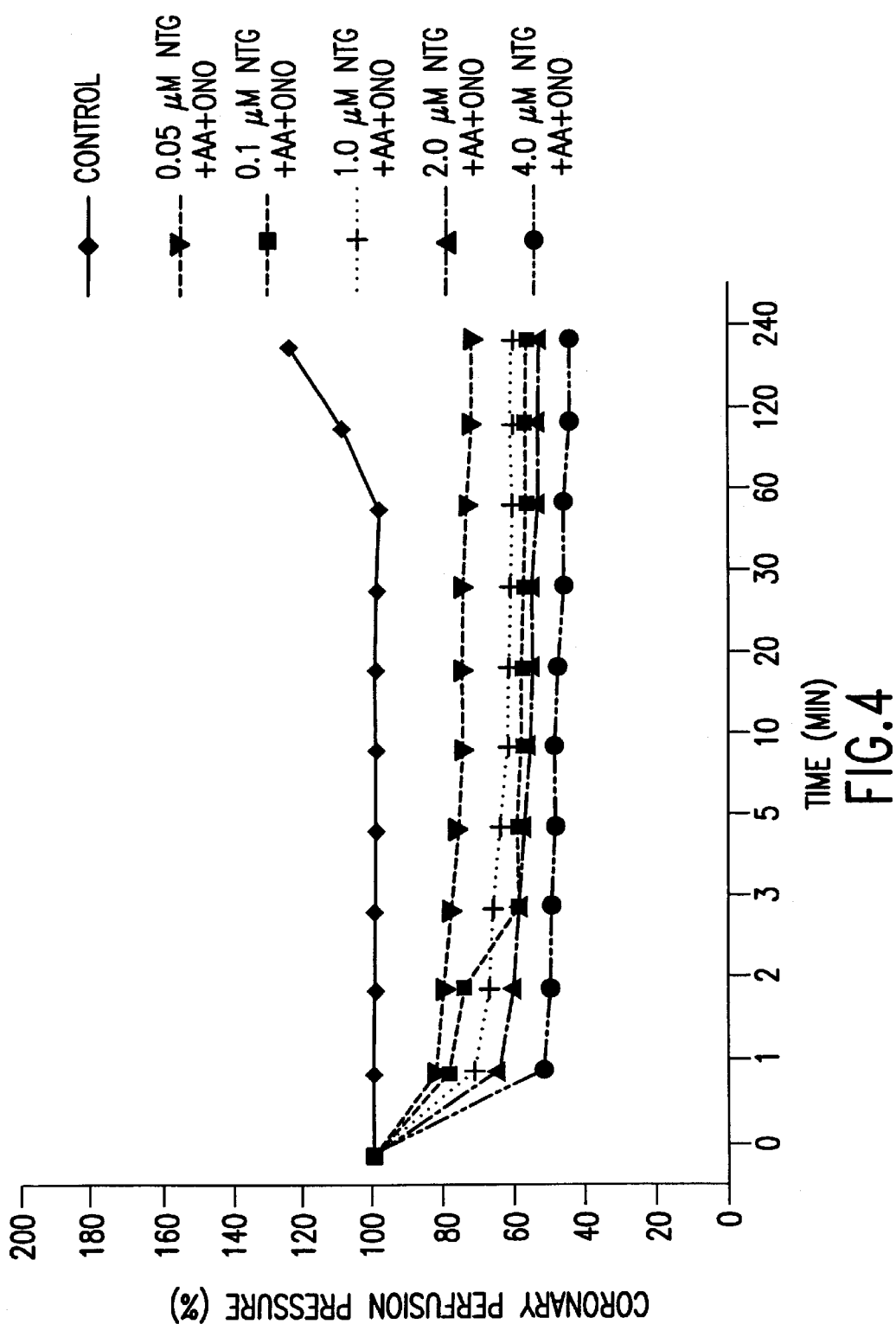
FIG. 4 is a line graph illustrating the effect on coronary perfusion pressure by varying concentrations of nitroglycerin administered with ONO-3708 and L-ascorbic acid.

As can be seen from FIG. 4 and Table 1, administering the organic nitrate, NTG, in conjunction with the synergistic composition containing 10 μM of ONO-3708 and 10 mM L-ascorbic acid (1:1000 molar ratio) greatly potentiated the NTG. The CPP rapidly dropped to 52% 1 minute after the administration of 4 μM of NTG and in conjunction with the L-ascorbic acid and ONO-3708 where it leveled off at 47% after 240 minutes (—●—). This compares with the transient drop of CPP after 1 minute to 94%, a gradual decrease to 84% after 3 minutes, followed by an increase of CPP to 150% after 240 minutes resulting from the administration of 4 μM of NTG alone (FIG. 1, —●—). Likewise, the combined administration of the three components provided a significant improvement over the co-administration of 4 μM NTG with ONO-3708 (FIG. 2, —▽—) which exhibited a CPP of 86% at 240 minutes and the co-administration of 4 μM NTG with L-ascorbic acid (FIG. 3, —○—) which exhibited a CPP of 76% at 240 minutes.

The synergistic composition also potentiated the effectiveness of low dosages of NTG, which provided no vasodilation when administered alone and only a slight decrease in CPP when co-administered with ONO-3708 or L-ascorbic acid. For example, the co-administration of 0.05 μM of NTG with L-ascorbic acid and ONO-3708 resulted a CPP of 77% five minutes after administration and 74% after 240 minutes (—▼—). Likewise, the co-administration of 0.1 μM of NTG with L-ascorbic acid and ONO-3708 resulted a CPP of 60% five minutes after administration and 59% after 240 minutes (—■—). However, the administration of either 0.05 μM NTG alone (FIG. 1, —▼—) or 0.1 μM NTG alone (FIG. 1, —■—) resulted in a CPP of 100% at best. The combination of ONO-3708 and L-ascorbic acid also provided a significant improvement over the co-administration of 0.05 μM NTG or 0.1 μM NTG with either ONO-3708 (FIG. 2, —■— and FIG. 2, —+—) or L-ascorbic acid (FIG. 3, —■— and FIG. 3, —+— which resulted in CPP values, at best, of 91% and 88%. Likewise, only a slight decrease in CPP was observed for the co-administration of ONO-3708 and L-ascorbic acid without NTG.

TABLE 1

CORONARY PERFUSION PRESSURE

| | 0 min | 1 min | 2 min | 3 min | 5 min | 10 min | 20 min | 30 min | 60 min | 120 min | 240 min |
|---|---|---|---|---|---|---|---|---|---|---|---|
| Control | 100 | 100 | 100 | 100 | 100 | 100 | 100 | 100 | 100 | 110 | 120 |
| NTG 0.05 μM | 100 | 100 | 100 | 100 | 100 | 100 | 100 | 100 | 100 | 109 | 112 |
| NTG 0.1 μM | 100 | 100 | 100 | 100 | 100 | 100 | 100 | 100 | 100 | 108 | 115 |
| NTG 2.0 μM | 100 | 98 | 97 | 96 | 98 | 99 | 100 | 102 | 104 | 114 | 115 |
| NTG 4.0 μM | 100 | 94 | 90 | 8 | 86 | 88 | 114 | 120 | 125 | 135 | 150 |
| NTG + 10 μM ONO-3708 | | | | | | | | | | | |
| 0.0 μM NTG | 100 | 96 | 94 | 92 | 92 | 92 | 92 | 92 | 92 | 92 | 92 |
| 0.05 μM NTG | 100 | 92 | 92 | 91 | 91 | 91 | 91 | 91 | 91 | 91 | 91 |
| 0.1 μM NTG | 100 | 94 | 93 | 92 | 92 | 92 | 92 | 92 | 92 | 92 | 92 |
| 1.0 μM NTG | 100 | 90 | 88 | 86 | 85 | 85 | 85 | 85 | 88 | 89 | 89 |
| 2.0 μM NTG | 100 | 86 | 84 | 82 | 80 | 80 | 80 | 80 | 88 | 89 | 92 |
| 4.0 μM | 100 | 82 | 81 | 79 | 79 | 79 | 79 | 79 | 85 | 86 | 86 |
| NTG + 10 mM L-Ascorbic Acid | | | | | | | | | | | |
| 0.0 μM NTG | 100 | 98 | 97 | 97 | 97 | 97 | 97 | 97 | 97 | 97 | 97 |
| 0.05 μM NTG | 100 | 94 | 92 | 91 | 90 | 89 | 86 | 88 | 88 | 88 | 88 |
| 0.1 μM NTG | 100 | 93 | 92 | 91 | 90 | 89 | 88 | 88 | 88 | 88 | 88 |
| 1.0 μM NTG | 100 | 90 | 90 | 88 | 87 | 86 | 85 | 83 | 82 | 82 | 82 |
| 2.0 μM NTG | 100 | 86 | 82 | 81 | 79 | 78 | 78 | 78 | 78 | 78 | 78 |
| 4.0 μM NTG | 100 | 87 | 87 | 76 | 76 | 76 | 76 | 76 | 76 | 76 | 76 |
| NTG + 10 μM ONO-3708 and 10 mM L-Ascorbic Acid | | | | | | | | | | | |
| 0.05 μM NTG | 100 | 82 | 80 | 78 | 77 | 76 | 76 | 76 | 75 | 74 | 74 |
| 0.1 μM NTG | 100 | 79 | 75 | 60 | 60 | 59 | 59 | 59 | 59 | 59 | 59 |
| 1.0 μM NTG | 100 | 72 | 68 | 67 | 65 | 63 | 63 | 63 | 63 | 63 | 63 |
| 2.0 μM NTG | 100 | 86 | 82 | 81 | 79 | 78 | 78 | 78 | 78 | 78 | 78 |
| 4.0 μM NTG | 100 | 52 | 51 | 51 | 50 | 50 | 49 | 48 | 48 | 47 | 47 |

Comparative Example 5

Following the procedure of Example 1, the effects of classic antioxidants on the vasodilating activity of NTG were ascertained. Two antioxidant composition were used: (a) TIRON 100 a membrane permeable free radical scavenger (active component-4,5-dihydroxy-1,3-benzenedisulfonic acid); and (b) superoxide dismutase ("SOD") a membrane impermeable free radical scavenger. 100 μM TIRON 100 and 80 U/mL SOD were administered alone to provide a control, and were co-administered separately with 4 μM NTG. The CPP results are listed in Table 2 below. The concentrations of TIRON 100 and SOD were selected since they are equivalents to 10 mM L-ascorbic acid in terms of free radical scavenging capacity. The free radical scavenging capacity of these compounds was determined by measuring the concentration required to scavenge all superoxide anions generated by purine and xanthine oxidase as detected by the reduction of ferrocytochrome to ferriccytochrome (I. Fridovich, 1970, J. Biol. Chem., 245, 4053–4057).

TABLE 2

| CORONARY PERFUSION PRESSURE | | | | | | | | | | | |
|---|---|---|---|---|---|---|---|---|---|---|---|
| | 0 min | 1 min | 2 min | 3 min | 5 min | 10 min | 20 min | 30 min | 60 min | 120 min | 240 min |
| 100 µM Tiron | | | | | | | | | | | |
| Control | 100 | 100 | 100 | 100 | 100 | 100 | 100 | 100 | 100 | 100 | 106 |
| 4 µM NTG + Tiron 100 80 U/mL SOD | 100 | 100 | 100 | 100 | 100 | 100 | 100 | 100 | 100 | 108 | 115 |
| Control | 100 | 100 | 100 | 100 | 100 | 100 | 100 | 100 | 100 | 104 | 108 |
| 4 µM NTG + SOD | 100 | 100 | 100 | 100 | 100 | 100 | 100 | 100 | 100 | 107 | 120 |

As can be seen from Table 2, neither antioxidant provided any potentiation of NTG. This data shows that the potentiation provided by L-ascorbic acid can be attributed to its reductive properties and not its ability to scavenge free radicals.

Example 6

Following the procedure of Example 1, the effects of non-antioxidant reducing agents in combination with thromboxane receptor antagonists on the vasodilating activity of NTG were ascertained. The CPP of hearts (n=2) perfused with 24 mL/min coronary flow 20 minutes after the stabilization period was deemed 100% and served as the control (A). Changes in CPP were calculated as percentage from the CPP of the control. After the stabilization period, separate groups of hearts (n 2) were perfused with an elevated flow for 10 minutes and the following drugs were administered for four hours: (B) 4 µM NTG, (C) 100 µM NADPH (reducing agent), (D) 4 µM NTG and 100 µM NADPH, (E) 10 µM ONO-3708, and (F) 4 µM NTG, 100 µM NADPH, and 10 µM ONO-3708. The NADPH concentration of 100 µM correlates intravenous dosage of about 642 µg/kg. The changes in the CPP were monitored and the CPP values 3 minutes after administration are shown in FIG. 5.

Figure 5:
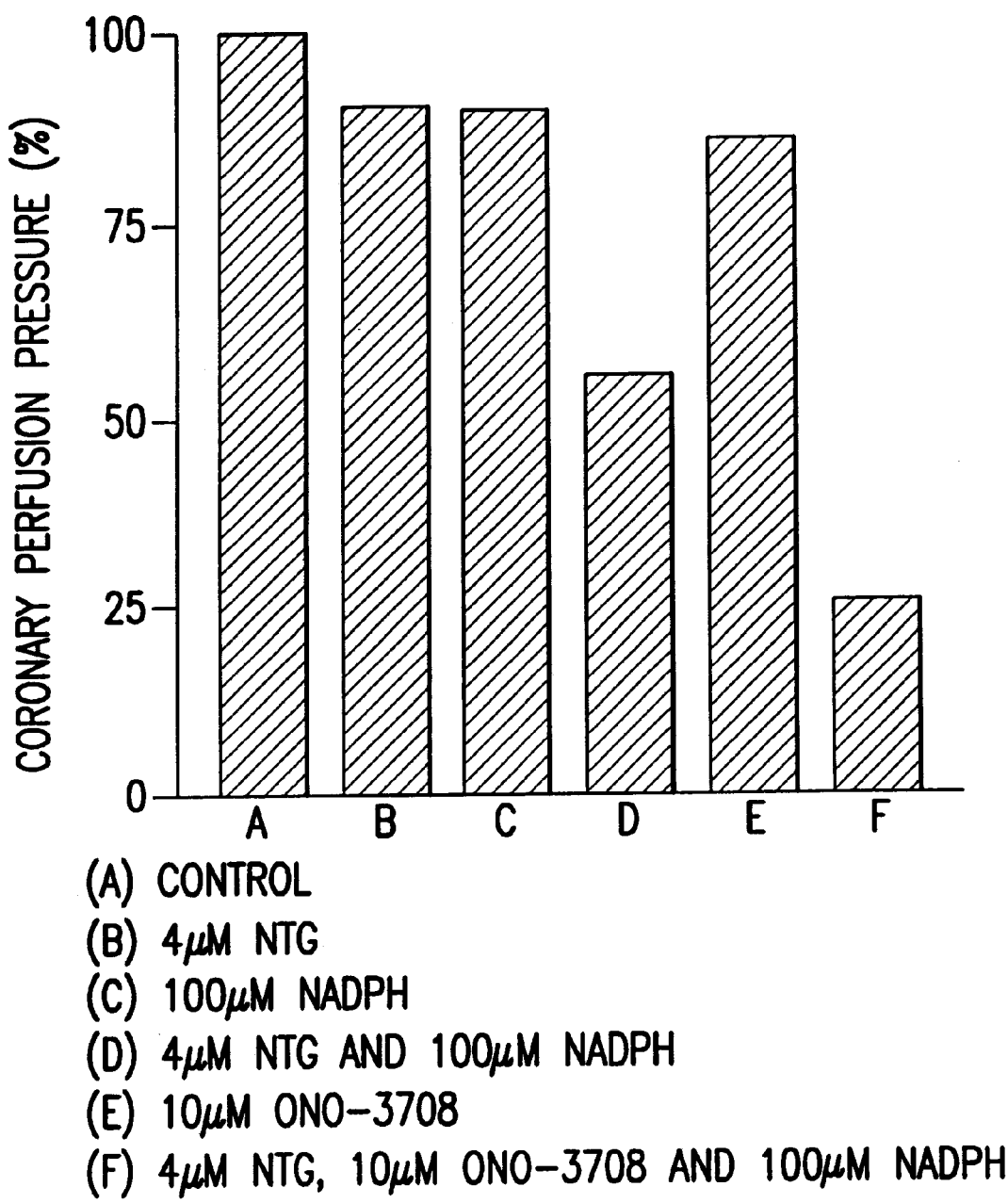
FIG. 5 is bar chart illustrating the effect on coronary perfusion pressure by the administration of nitroglycerin, ONO-3708, NADPH as a reducing agent, and various combinations of the compounds.

From FIG. 5, it is readily apparent that the co-administration of a thromboxane receptor antagonist, ONO-3708, and a non-antioxidant reducing agent, NADPH, are effective in potentiating the vasodilating activity of organic nitrates such as NTG. For example, 4 µM NTG administered alone (B) resulted in a CPP of 87%. NADPH administered alone (C) resulted in a CPP of 85%. ONO-3708 administered alone (E) resulted in a CPP of 82%. However, when the NTG was co-administered with NADPH and ONO-3708 (F), a CPP of 25% resulted. This dramatic drop in CPP illustrates the synergistic potentiation of organic nitrates such as NTG using thromboxane receptor antagonists and reducing agents. Moreover, the reduced levels were maintained for the remainder of the experiment. Similar results were obtained with sodium dithionate (1 mM) and sodium pyruvate (10 mM).

Example 7

Following the procedure of Example 6, the effects on the vasodilating activity of NTG by co-administering the thromboxane receptor antagonist Seratrodast with L-ascorbic acid were ascertained. The following compounds were perfused in separate groups of hearts (n=2) for up to four hours: (A) no compounds—control; (B) 4 µM NTG, (C) 50 µM Seratrodast, (D) 4 µM NTG and 50 µM Seratrodast, and (E) 4 µM NTG, 50 µM Seratrodast, and 10 mM L-ascorbic acid. The 50 µM Seratrodast concentration is the $IC_{50}$ for suppressing vasoconstriction induced with U 46619, a thromboxane $A_2$ receptor analogue. This concentration correlates to an intravenous dosage about 900 µg/kg. CPP values after 3 minutes of administration are shown in FIG. 6.

Figure 6:
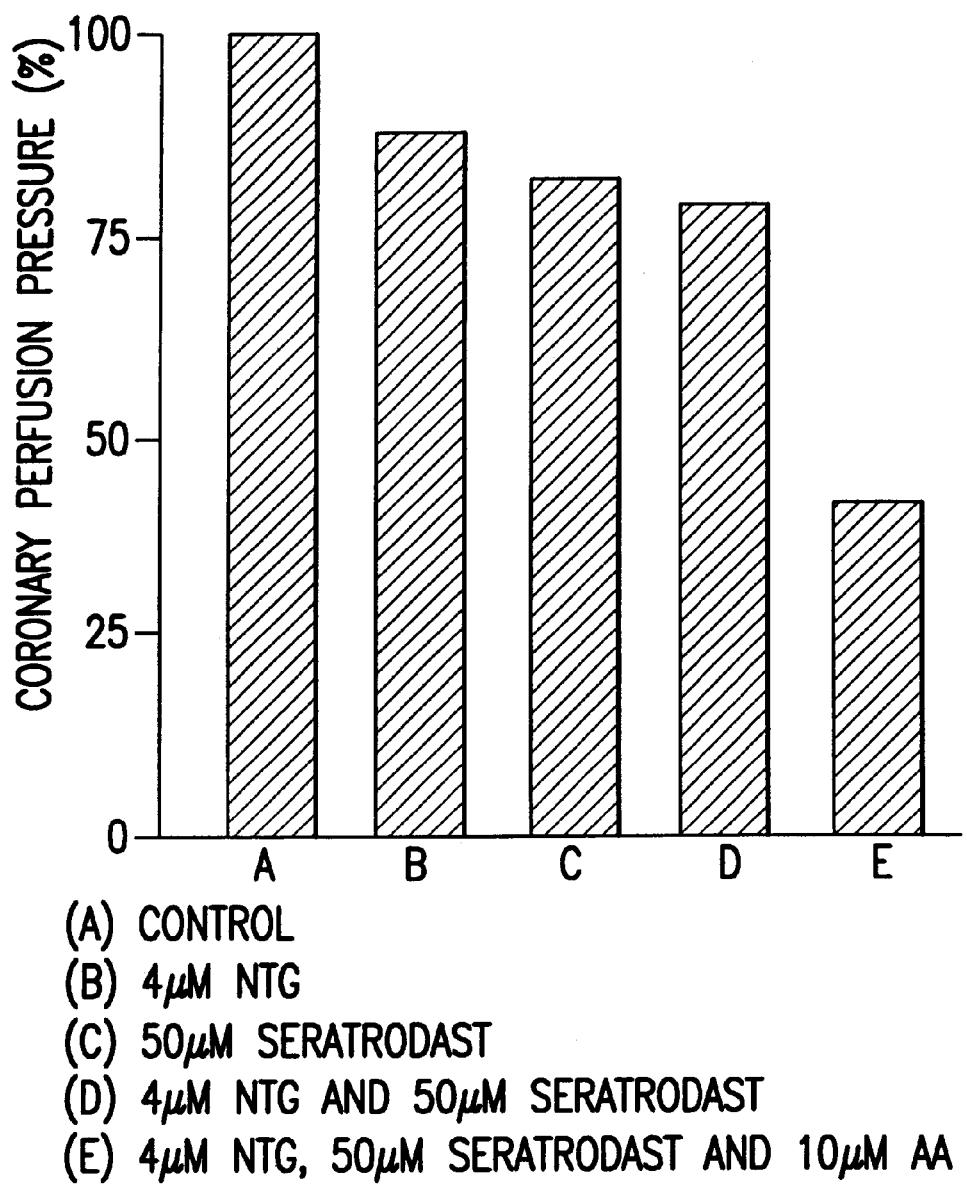
FIG. 6 is a bar chart illustrating the effect on coronary perfusion pressure by the administration of nitroglycerin, L-ascorbic acid, a thromboxane receptor antagonist, Seratrodast, and various combinations of the compounds.

As shown in the FIG. 6, the thromboxane receptor antagonist, Seratrodast, when combined with L-ascorbic acid synergistically potentiates the vasodilating effect of organic nitrates such as NTG. For example, 4 µM NTG administered alone (B) resulted in a CPP of 85%. Seratrodast administered alone (C) resulted in a CPP of 82%. Seratrodast administered alone (D) resulted in a CPP of 77%. However, when the NTG was co-administered with L-ascorbic acid and Seratrodast (E), a CPP of 43% resulted. These reduced CPP values were maintained for the remainder of the experiment.

It will be apparent to those skilled in the art that various modifications and variations can be made without departing from the spirit or scope of the invention. Thus, it is intended that the present invention cover the modifications and variations of this invention, provided they come within the scope of the appended claims and their equivalents.

What is claimed is:

1. A method for potentiating an organic nitrate having vasodilating activity, which comprises administering to a subject an effective amount of said organic nitrate with a potentiating amount of a thromboxane receptor antagonist and a reducing agent.

2. The method of claim 1, wherein said organic nitrate, said thromboxane receptor antagonist and said reducing agent are co-administered to said subject.

3. The method of claim 1, wherein said thromboxane receptor antagonist and said reducing agent are administered to said subject prior to the administration of said organic nitrate.

4. The method of claim 1, wherein said organic nitrate is administered to said subject prior to the administration of said thromboxane receptor antagonist and said reducing agent.

5. The method of claim 1, wherein said organic nitrate having vasodilating activity is selected from the group consisting of nitroglycerin, amyl nitrite, isosorbide dinitrate, isosorbide mononitrate, erythrityl tetranitrate, pentaerythritol trinitrate, pentaerythritol tetranitrate, sodium nitroprusside, trolnitrate phosphate, clonitrate, mannitol hexanitrate, propatyl nitrate, and mixtures thereof.

6. The method of claim 1, wherein said organic nitrate having vasodilating activity is nitroglycerin.

7. The method of claim 1, wherein said reducing agent is a non-antioxidant reducing agent.

8. The method of claim 7, wherein said non-antioxidant reducing agent is selected from the group consisting of GDP, GTP, NADPH, NADH, $FADH_2$, $FMNH_2$, sodium pyruvate, sodium dithionite, N-acetylcysteine, reduced glutathione and mixtures thereof.

9. The method of claim 1, wherein said reducing agent is L-ascorbic acid.

10. The method of claim 1, wherein said thromboxane receptor antagonist is selected from the group consisting of ONO-3708, Seratrodast, Rodigrel, Daltroban, Sulotroban, AH 23848, GR 32191, ICI 192605, SQ 28668, SQ 28913, SQ 29548, and mixtures thereof.

11. The method of claim 1, wherein said thromboxane receptor antagonist is ONO-3708.

12. The method of claim 1, wherein said thromboxane receptor antagonist is Seratrodast.

13. The method of claim 1, wherein said potentiating amount of provides at least a 15% decrease in coronary perfusion pressure to said subject as compared to the administration of said organic nitrate alone.

14. The method of claim 13, wherein said potentiating amount provides at least a 25% decrease in coronary perfusion pressure.

15. The method of claim 14, wherein said potentiating amount provides at least a 40% decrease in coronary perfusion pressure.

16. The method of claim 1, wherein said subject is a mammal.

17. The method of claim 16, wherein said mammal is in need of vasodilation.

18. The method of claim 17, wherein said mammal exhibits a tolerance for said organic nitrate.

19. The method of claim 1, wherein said effective amount of said organic nitrate is 0.0001 to 120 mg/kg of body weight.

20. The method of claim 19, wherein said effective amount is 0.0001 to 30 mg/kg.

21. The method of claim 20, wherein said effective amount is 0.0001 to 0.5 mg/kg.

22. A formulation for inducing vasodilation comprising:
   (i) an effective amount of an organic nitrate having vasodilating activity; and
   (ii) a potentiating amount of a thromboxane receptor antagonist and a reducing agent.

23. The formulation of claim 22, wherein said organic nitrate is selected from the group consisting of nitroglycerin, amyl nitrite, isosorbide dinitrate, isosorbide mononitrate, erythrityl tetranitrate, pentaerythritol trinitrate, pentaerythritol tetranitrate, sodium nitroprusside, trolnitrate phosphate, clonitrate, mannitol hexanitrate, propatyl nitrate, and mixtures thereof.

24. The formulation of claim 22, wherein said organic nitrate is nitroglycerin.

25. The formulation of claim 22, wherein said reducing agent is non-antioxidant reducing agent.

26. The formulation of claim 25, wherein said non-antioxidant reducing agent is selected from the group consisting of GDP, GTP, NADPH, NADH, $FADH_2$, $FMNH_2$, sodium pyruvate, sodium dithionite, N-acetylcysteine, reduced glutathione, and mixtures thereof.

27. The formulation of claim 22, wherein said reducing agent is L-ascorbic acid.

28. The formulation of claim 22, wherein said thromboxane receptor antagonist is selected from the group consisting of ONO-3708, Seratrodast, Rodigrel, Daltroban, Sulotroban, AH 23848, GR 32191, ICI 192605, SQ 28668, SQ 28913, SQ 29548, and mixtures thereof.

29. The formulation of claim 22, wherein said thromboxane receptor antagonist is ONO-3708.

30. The formulation of claim 22, wherein said thromboxane receptor antagonist is Seratrodast.

31. The formulation of claim 22, wherein said potentiating amount is an organic nitrate:thromboxane receptor antagonist ratio of 1:11 to 1:2000, and an organic nitrate:reducing agent ratio of 1:10 to $1:5 \times 10^7$.

32. The formulation of claim 31, wherein said organic nitrate:thromboxane receptor antagonist ratio is 1:1 to 1:1000, and said organic nitrate:reducing agent ratio is 1:10 to $1:5 \times 10^5$.

33. The formulation of claim 32, wherein said organic nitrate:tromboxane receptor antagonist ratio is 1:1 to 1:100, and said organic nitrate:reducing agent ratio is 1:10 to $1:5 \times 10^3$.

34. The formulation of claim 22, further comprising a physiologically-acceptable carrier.

35. A synergistic composition for potentiating an organic nitrate having vasodilating activity, comprising a thromboxane receptor antagonist and a reducing agent.

36. The composition of claim 35, wherein said reducing agent is non-antioxidant reducing agent.

37. The composition of claim 36, wherein said non-antioxidant reducing agent is selected from the group consisting of GDP, GTP, NADPH, NADH, $FADH_2$, $FMNH_2$, sodium pyruvate, sodium dithionite, N-acetylcysteine, reduced glutathione and mixtures thereof.

38. The composition of claim 35, wherein said reducing agent is L-ascorbic acid.

39. The composition of claim 35, wherein said thromboxane receptor antagonist is selected from the group consisting of ONO-3708, Seratrodast, Rodigrel, Daltroban, Sulotroban, AH 23848, GR 32191, ICI 192605, SQ 28668, SQ 28913, SQ 29548, and mixtures thereof.

40. The composition of claim 35, wherein said thromboxane receptor antagonist is ONO-3708.

41. The composition of claim 35, wherein said thromboxane receptor antagonist is Seratrodast.

42. The composition of claim 35, wherein said thromboxane receptor antagonist and said reducing agent are in a ratio ranging from 1:1 to $1:5 \times 10^7$.

43. The composition of claim 42, wherein said ratio ranges from 1:1 to $1:5 \times 10^5$.

44. The composition of claim 43, wherein said ratio ranges from 1:1 to $1:5 \times 10^3$.

45. The composition of claim 35, further comprising a physiologically-acceptable carrier.

* * * * *